United States Patent [19]

Deutsch

[11] Patent Number: 5,026,829
[45] Date of Patent: Jun. 25, 1991

[54] CYCLO SUBSTITUTED PROPYLENEAMINE OXIME AND ITS USE AS A BRAIN IMAGING AGENT

[75] Inventor: Edward A. Deutsch, Cincinnati, Ohio

[73] Assignee: University of Cincinnati, Cincinnati, Ohio

[21] Appl. No.: 453,696

[22] Filed: Dec. 20, 1989

Related U.S. Application Data

[62] Division of Ser. No. 300,617, Jan. 23, 1989, Pat. No. 4,895,960.

[51] Int. Cl.$^5$ .................. A61K 43/00; C07F 13/00
[52] U.S. Cl. ...................................... 534/14; 424/1.1; 424/9; 422/61; 206/569
[58] Field of Search .................. 424/1.1, 9; 534/14, 534/10

[56] References Cited

U.S. PATENT DOCUMENTS

| | | | |
|---|---|---|---|
| 4,615,876 | 10/1986 | Troutner et al. | 424/1.1 |
| 4,714,605 | 12/1987 | Feld et al. | 424/1.1 |
| 4,789,736 | 12/1988 | Canning et al. | 534/14 |
| 4,818,813 | 4/1989 | Nowotnik et al. | 534/14 |
| 4,895,960 | 1/1990 | Deutsch | 534/14 X |

FOREIGN PATENT DOCUMENTS

| | | |
|---|---|---|
| 123504 | 10/1984 | European Pat. Off. .............. 534/14 |
| 179608 | 8/1986 | European Pat. Off. . |
| 194843 | 9/1986 | European Pat. Off. . |

OTHER PUBLICATIONS

Hung et al., *J. Nucl. Med.*, 29:1568–1576 (1988).
35th Annual Meeting, *J. Nucl. Med.*, vol. 29, No. 5, May 1988.

Primary Examiner—Robert L. Stoll
Assistant Examiner—John M. Covert
Attorney, Agent, or Firm—Wood, Herron & Evans

[57] ABSTRACT

A useful brain perfusion imaging agent comprises

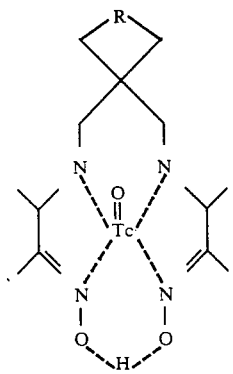

wherein R completes a four or five member ring. The agent is stable in vitro permitting its use up to six to eight hours after preparation.

4 Claims, No Drawings

CYCLO SUBSTITUTED PROPYLENEAMINE OXIME AND ITS USE AS A BRAIN IMAGING AGENT

This is a division, of application Ser. No. 300,617, filed Jan. 23, 1989, now U.S. Pat. No. 4,895,960.

BACKGROUND OF THE INVENTION

It is extremely difficult to obtain a chemical agent which will successfully image in the brain. The agent must pass through the blood brain barrier and then be retained in the brain. Although there are many compositions which do pass through the blood brain barrier there are very few that do not quickly clear from the brain by passing back through the blood brain barrier. It is theorized that in order for an agent to remain within the brain to provide a successful image some chemical alteration of the agent must occur within the brain.

Hexamethylpropylene diamine oxime (4,8,-diaza-3,6,6,9-tetramethyl undecane-2,10-dione bisoxime) hereinafter referred to as HM-PAO has been found to be very useful as a brain perfusion imaging agent. It is believed that the inherent instability of HM-PAO ligated to 99m-technetium in some way causes this agent to be chemically altered in the brain. Thus, 99m-Tc HM-PAO passes through the blood brain barrier, is theoretically altered in some way, and remains in the brain for a period of time sufficient to obtain a successful brain image.

There are several patents which discuss and disclose this composition. For example, Troutner et al U.S. Pat. No. 4,615,876, European Patent Application No. 0 179 608 published April 30, 1986, European Patent Application No. 0 123 504 published Oct. 31, 1984 and U.S. Pat. No. 4,789,736. Unfortunately, the in vivo instability of this composition which makes it a successful brain imaging agent also makes it a very unstable composition in vitro. In an article entitled "Kinetic Analysis of Technetium-99m D,l-HM-PAO Decomposition in Aqueous Media," *J. Nucl. Med.*, 29:15681576, 1988, it is reported that although the aqueous in vitro degradation rate of this complex is slow the instability of the technetium bonded HM-PAO in vitro requires that it be administered within 30 minutes of its formulation. In the proceedings of the 35th Annual Meeting of the J. Nucl. Med., Vol. 29, No. 5, May, 1988 it is reported that the technetium complex of the HM-PAO can be stabilized by using gentisic acid within the first 30 seconds after formation of the technetium complex. However, even with this modification, this radiopharmaceutical must be used within hours after preparation.

SUMMARY OF THE INVENTION

Accordingly, it is an object of the present invention to provide a useful brain imaging agent which successful crosses the blood brain barrier and remains in the brain for a period of time to permit successful brain imaging. Further, it is an object of the present invention to provide such a complex wherein the in vitro stability of the technetium complex agent is sufficiently increased so that it need not be applied within the first couple of hours of preparation. Accordingly, the present invention provides a complex having the following general formula:

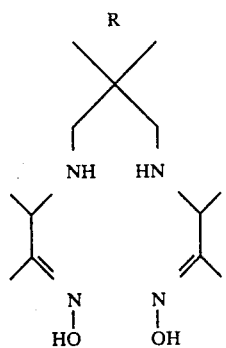

wherein R represents $-CH_2-$, $-CH_2-CH_2-$, $-O-$, $-S-$ or $-NR'-$ where R' is $C_1-C_{12}$ alkyl. The objects and advantages of the present invention will be further appreciated in light of the following detailed description.

DETAILED DESCRIPTION OF THE INVENTION

A brain perfusion imaging agent is formed by complexing pertechnetate to a tetraamine ligand. The tetraamine ligand has the following general formula:

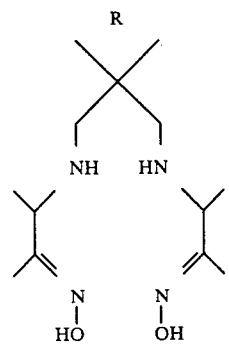

Formula 1 wherein R represents a bivalent radical which completes a four or five member ring. R specifically can represent $-CH_2-$ (methylene), $-CH_2-CH_2-$ (ethylene), $-O-$ (ether), $-S-$ (sulfide) or $-NR'-$ (secondary amine) where R' represents H or $C_1-C_{12}$ alkyl. This ligand exists in d,l and meso isomeric forms. Only the d,l isomer is useful in the present invention. The ligand can then be complexed to technetium to give a complex of the following general formula:

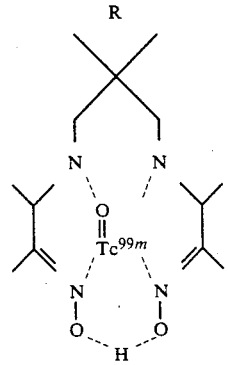

Formula 2

The ligand is formed by reacting 2.3 butanedione monoxime with a cyclic diamine having the following general formula:

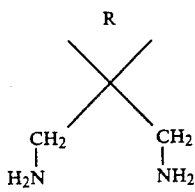

Formula 3

The product is then reduced with sodium borohydride to form the ligand of the present invention.

The reaction will be further appreciated in light of the following detailed description of the formation of 4,8-diaza-3,9-dimethyl-6,6-(trimethylene)undecane-2,10-dione bis oxime (CB-PAO) wherein R of formula 1 and 2 represents methylene. The bis amine which is reacted with the 2,3-butanedione monoxime is formed from 1,1-cyclobutanedicarboxylic acid. Into a 300 milliliter flask were successively added 60ml of absolute benzene, 4.8g (33mmol) of 1,1-cyclobutane dicarboxylic acid and a trace (20μl) of pyridine, and then 8.7g (68mmol) of oxalyl chloride. The reaction temperature was maintained at 30-45° C., and the reaction was continued until bubbling from the reaction mixture ceased. Ammonia gas was then bubbled into the reaction mixture for about one hour with stirring and cooling. The solvents were subsequently removed under vacuum and the resulting white precipitate was washed twice with water. The product thus obtained was recrystallized from boiling water-methanol solution (50:50v/v), giving 4.2g (yield, 91%) of a product melting at 265-268° C. This product is the 1,1-cyclobutanedicarboxyamide.

This was then reacted with lithium aluminum hydride to form the diamine. Specifically into a 100 milliliter three necked flask 46ml (0.046mol) of a 1.0M solution of LiAlH4 in THF was added and brought to reflux; 1.0g (0.007mol) of ground diamide suspended in 20ml of THF was then added slowly. The mixture was refluxed for one hour then cooled to room temperature. To the cooled reaction mixture were added successively with stirring 1.ml of water, 1.ml of 6N NaOH and then 5.1ml of water. Stirring was continued for 20 minutes. The resulting precipitate was removed by filtration and carefully washed three times with 20ml of ether. The filtrate was concentrated to 10ml and then 30ml of 1N HCl solution in ether was added to immediately yield a white precipitate of diamine dihydrochloride (0.95g, 73%). Seven grams of the crude diamine dihydrochloride from several preparations was neutralized with 13 ml of 6N NaOH and the free diamine was purified by fractional distillation. The yield was 2.5g of distilled product, boiling point 97-99° C. at about 25mm Hg. The product was 1,1-cyclobutanedimethyleneamine (diamine).

A bis imine was then formed by reacting the diamine with 2.3-butanedione monoxime purchased from Matheson Company. Specifically in a 300ml three necked flask with a Dean-Stark trap, 4.7g (0.047mol) of butanedione monoxime was dissolved in 52 ml of absolute benzene containing two drops (20ul) of acetic acid and the resulting solution was brought to reflux. Then a solution of 2.5g (0.021mol) of diamine dissolved in 50ml of absolute benzene was added over a period of three hours under an argon atmosphere. The resulting yellow-brown solution was refluxed for ten hours, then allowed to cool to room temperature and stored at 4° C. for forty hours. The resulting solid was removed by filtration and washed with a little cold (−40° C.) acetonitrile. The yield of the crude bis-imine was 3.8g.

To form the CB-PAO this formed bis imine was then reduced with sodium borohydride. Specifically, in a 100 milliliter three necked flask, 3.3g (0.0118mol) of bis imine was slurried in 98% aqueous ethanol (30ml) 0° C. Sodium borohydride (0.5g (0.013mol)) was added in proportions over 20 minutes, the resulting mixture was stirred at 0° C. for two hours and then 10ml of water was added. The mixture was stirred well for two additional hours at room temperature. The ethanol was then removed under vacuum and more water (7ml) was added. The pH was adjusted to about 11 and then the formed white solid was removed by filtration and washed with water and dried in vacuo.

The product obtained had both the meso and the d,l-isomers of CB-PAO. The d,l isomer is the isomer used for brain perfusion imaging. Accordingly, a sample of the crude CB-PAO obtained directly from the aqueous work-up described above was recrystallized five times from hot acetonitrile using 50 ml of acetonitrile per gram of crude CB-PAO. Subsequent 65 ml per gram was used for the second and 80 ml per gram of CB-PAO for the third, fourth and fifth recrystallizations. This yields the pure meso isomer as fine white needles (melting point 155-156 and 30% yield).

The first three filtrates were collected and brought to dryness under vacuum to yield a product with a meso:d,l ratio of about 30:70. This product was then recrystallized from ethyl acetate using 40 ml of ethyl acetate per gram of d,l enriched product. One small crop of crystals (ratio of meso:d,l 50:50) was removed, and the filtrate was concentrated to about the point where there was about 30ml solvent per gram of CB-PAO and another small crop of crystals (ratio of meso:d,l equals 40:60) was removed. After this filtrate was diluted to a point where there was about 30-40ml solvent per gram of CB-PAO (ratio of meso:d,l equals 15:85), crystallization was again effected to yield the pure d,l isomer. The filtrate was concentrated then recrystallized to yield a second crop of d,l isomer. At this point the yield of d,l isomer is about 10-15%. Repetition of the above procedure allows the yield to approach 20%. The following product was obtained:

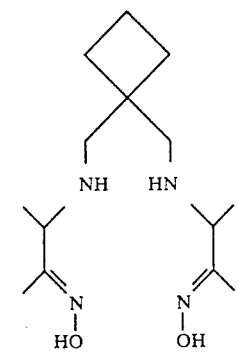

The d,l isomer is then complexed with 99m-technetium to obtain a brain perfusion imaging agent. To formulate the 99m-Tc-d,l-CB-PAO 5ml of a ligand solution is placed into an evacuated 10 ml vial. The ligand solution contained approximately 0.5 mg/ml of ligand. One hundred and fifty microliters of a tin chloride solution containing 10 mg of tin chloride per 50 ml in water was added. Ten to one hundred microliters of 99m-pertechnetate sodium solution eluted from a molybdenum 99 generator is added to the vial and this is shaken for 10 seconds. An imaging solution can be immediately removed for use.

However, it is preferable that the pH of the solution which upon addition of the stanous chloride was about 8.9 be lowered. Accordingly, gentisic acid was used to lower the pH of the complex. A solution of gentisic acid was made by dissolving 0.0303g of gentisic acid and 30ml saline. 3.0 milliliters of this solution was pipetted into another vial.

An additional 30ml of saline was added. This latter vial was purged with argon for 50 minutes and sealed to yield a solution of about 6mM in gentisic acid. 1.0–1.2ml of the above solution was added to a 10 ml evacuated vial. 2.5 milliliters of 99m-Tc-CB-PAO previously prepared is then added to this evacuated vial. This was then tested for stability. At 15 minutes, 100% of the 99m-Tc-CB-PAO remained. At 165 minutes again 100% of the 99m-Tc-CB-PAO remained. At 18 hours 98% of the 99m-Tc-CB-PAO remained.

A kit for practicing the present invention would contain a first vial which would include sterile lypholized mixture of 0.5ml d,l-CB-PAO, 0.0075ml stanous tartrate and 0.9ml sodium chloride. A second vial would contain sterile lypholized 10ml of an antioxidant such as sodium ascorbate or sodium gentisate brought to pH 7.4 with a phosphate buffer.

For use, vial 2 would be reconstituted with 1.0 ml sterile saline and the resulting solution would be taken up into a sterile syringe. Vial 1 would then be reconstituted with 4 ml of 99m-pertechnetate (usually 10–150-mCi) and shaken for 30 seconds. The contents of vial 2 are then immediately injected into vial 1 while sterile conditions are maintained throughout by usual means. Vial 1 would then contain the brain imaging agent of the present invention.

The obtained ligated 99m-Tc agent is intravenously injected into the patient under study. Usually 10–150 mCi of activity is injected. After a few minutes, the patient's brain can be imaged using either a normal planar gamma ray detection camera or a SPECT (Single Photo Emission Computed Tomography) device which yields three dimensional images.

In order to test the in vitro stability of the 99m-Tc-CB-PAO, 99m-Tc-CB-PAO and 99m-Tc-HMPAO were prepared in the same vial. The CB-PAO and HM-PAO agents were both reacted with pertechnetate in the same vial. This insures that both compositions were subjected to the same characteristics. These were then tested using HPLC. The results showing the percentage of 99m-Tc CB-PAO (labeled CB) and 99m-Tc HM-PAO labeled HM are shown in Table 1 over a period of 0 minutes to 13.4 hours. At 13.4 hours most of the 99m-Tc HM-PAO had decomposed whereas most of the 99m-Tc CB-PAO remained.

TABLE 1

| Time | CB | HM | CB/HM | Stabilization |
|---|---|---|---|---|
| 0 | 55.2 | 39.5 | 1.40 | 0% |
| 23 min | 55.4 | 29.9 | 1.85 | 30% |
| 74 min | 57.9 | 28.4 | 2.04 | 50% |
| 3.3 h | 58.1 | 27.5 | 2.11 | 53% |
| 12.2 h | 38.5 | 11.7 | 3.29 | 140% |
| 13.4 h | 34.8 | 9.7 | 3.58 | 160% |

This establishes that the 99m-Tc CB-PAO of the present invention is substantially more stable in vitro than the prior art brain imaging agent.

This was then tested to show that it maintained its efficacy in vivo. In order to test the whole body biodistribution of the 99m-Tc CB-PAO tracer, three normal human volunteers were tested using single photon emission computed tomography. Whole body images were obtained at 15 minutes, two hours and five hours after an intraveneous injection of about 13 millicurries of Tc-99m d,l-CB-PAO. A dynamic study during the first ten minutes after administration of the tracer defined the time activity curve for brain uptake. The tomographic study was performed at one hour after administration. Venous blood samples were collected at various times up to five hours after administration and urine was collected up to 24 hours after administration.

Approximately 3.6% of the injected dose is taken up by the brain within the first five minutes after injection and this is stable for up to five hours. The decrease in cerebral activity is only about 5% between 15 minutes and 2 hours after injection. Approximately 24% of the injected dose is cleared through the renal system within five hours and approximately 37% is cleared within 24 hours. Tomographic brain images show good definition of cerebral structures and good distinction between grey and white matter. The whole body distribution at fifteen minutes, two hours and five hours is shown in Table 2.

TABLE 2

| ORGAN | 15' | 2h | 5h |
|---|---|---|---|
| Brain | 3.6 ± 0.26 | 3.5 ± 0.15 | 3.5 ± 0.11 |
| Lungs | 4.0 ± 0.85 | 3.1 ± 0.70 | 2.7 ± 0.72 |
| Liver | 26.4 ± 7.1 | 25.4 ± 7. | 22.3 ± 9.5 |
| Gallbladder | 2.2 ± 0.05 | 2.8 ± 0.7 | 1.7 ± 0.65 |
| Bladder & Urine | 4.2 ± 1.36 | 19.4 ± 8.4 | 23.5 ± 2.80 |
| Blood | 14.9 ± 0.79 | 8.3 ± 0.7 | 5.8 ± 0.45 |

Thus, the present invention provides a kit for providing a technetium brain perfusion imaging agent or tracer which is stable in vitro and performs well as a brain imaging agent, i.e., passes the blood brain barrier entering the brain and remains there for a protracted period of time.

The preceding has been a description of the present invention as well as the preferred embodiment currently known for practicing the invention. However, the invention should be defined only by the appended claims wherein I claim:

1. A brain perfusion imaging agent having the following general formula:

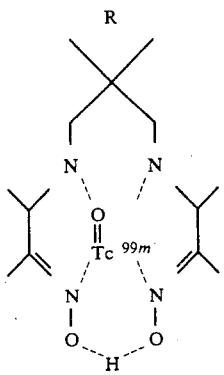

wherein R represents a bivalent radical completing a four or five member ring and is selected from the group consisting of ethylene, methylene, ether, sulfide, secondary amine and $C_1$–$C_{12}$ substituted tertiary amine.

2. The brain perfusion imaging agent claimed in claim 1 wherein R represents methylene.

3. A method of obtaining a brain image of a patient comprising:

injecting an effective amount of the composition claimed in claim 1 into a patient;

detecting the concentration and location of said agent within said brain.

4. A kit comprising:

a first vial containing a lyophilized ligand having the following general formula:

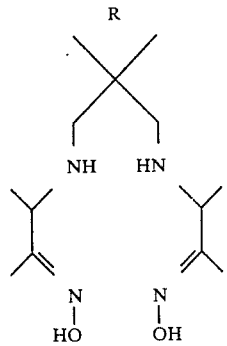

wherein R represents a bivalent radical completing a four or five member ring and is selected from the group consisting of ethylene, methylene, ether, sulfide, secondary amine and $C_1$–$C_{12}$ substituted tertiary amine and an effective amount of a reducing agent;

a second vial containing an effective amount of lyophilized buffered antioxidant selected from the group consisting of sodium gentisate and sodium ascorbate.

* * * * *